US012631649B2

(12) United States Patent
Chen et al.

(10) Patent No.: US 12,631,649 B2
(45) Date of Patent: May 19, 2026

(54) METHOD FOR MULTIDIMENSIONAL EVALUATION OF THE SIMILARITY OF SAMPLES TO BREAST MILK

(71) Applicant: Beijing Sanyuan Foods Co., Ltd., Beijing (CN)

(72) Inventors: Lijun Chen, Beijing (CN); Qian Liu, Beijing (CN); Yan Liu, Beijing (CN); Junying Zhao, Beijing (CN); Bin Liu, Beijing (CN); Yan Liu, Beijing (CN); Weicang Qiao, Beijing (CN); Minghui Zhang, Beijing (CN); Yaling Wang, Beijing (CN); Xiaofei Fan, Beijing (CN); Ziqi Li, Beijing (CN)

(73) Assignee: BEIJING SANYUAN FOODS CO., LTD., Beijing (CN)

( * ) Notice: Subject to any disclaimer, the term of this patent is extended or adjusted under 35 U.S.C. 154(b) by 471 days.

(21) Appl. No.: 18/476,234

(22) Filed: Sep. 27, 2023

(65) Prior Publication Data

US 2024/0345098 A1      Oct. 17, 2024

Related U.S. Application Data

(63) Continuation of application No. PCT/CN2023/101851, filed on Jun. 21, 2023.

(30) Foreign Application Priority Data

Apr. 13, 2023      (CN) .......................... 202310396931.7

(51) Int. Cl.
*G01N 33/68* (2006.01)
*G01N 30/06* (2006.01)

(52) U.S. Cl.
CPC ......... *G01N 33/6848* (2013.01); *G01N 30/06* (2013.01)

(58) Field of Classification Search
CPC ..... G01N 30/06; G01N 33/6848; G01N 33/92
See application file for complete search history.

(56) References Cited

FOREIGN PATENT DOCUMENTS

CN        115267098 A   * 11/2022   ............. G01N 33/06
CN        116106231 A      5/2023

* cited by examiner

*Primary Examiner* — Jennifer Wecker
(74) *Attorney, Agent, or Firm* — HAUPTMAN HAM, LLP

(57)      ABSTRACT

The present invention relates to a method for multidimensional evaluation of the similarity of a sample to breast milk, wherein the method is performed in the following steps: (1) establishing a local breast milk phospholipid database; (2) collecting and pretreating a sample to be evaluated; (3) determining the contents of characteristic phospholipid subclasses, the contents of characteristic phospholipid molecules in the sample to be evaluated, and obtaining a microstructural image of milk fat globules in the sample by confocal laser scanning microscopy; (4) calculating the score G for the sample to be evaluated. The present invention evaluates the similarity of samples to breast milk based on phospholipids in three aspects: the composition of characteristic phospholipid subclasses, the composition of characteristic phospholipid molecules, and the morphological similarity evaluation, so that the scheme can better evaluate the simulation quality of infant formulas and their raw and auxiliary materials to breast milk based on phospholipids.

12 Claims, 3 Drawing Sheets

Nile red stained images

Rd-DOPE stained images

Breast milk group

Group of improved infant formula added with phospholipids

Group of common infant formula

Nile red stained images

Rd-DOPE stained images

Breast milk group

Group of improved infant formula added with phospholipids

Group of common infant formula

Duodenum

Jejunum

Ileum

Colon

Fed with breast milk

Fed with common infant formula

Fed with improved infant formula added with phospholipids

1

METHOD FOR MULTIDIMENSIONAL EVALUATION OF THE SIMILARITY OF SAMPLES TO BREAST MILK

CROSS-REFERENCE

The present application is a Continuation of International Application No. PCT/CN2023/101851 filed Jun. 21, 2023, and claims priority to Chinese patent application No. 202310396931.7 filed at the China Patent Office on Apr. 13, 2023, and entitled "method for multidimensional evaluation of the similarity of samples to breast milk", the contents of which are incorporated by reference herein in their entireties.

TECHNICAL FIELD

The present invention relates to the field of dairy product evaluation, and in particular to a method for multidimensional evaluation of the similarity of samples to breast milk.

BACKGROUND ART

Breast milk is enriched in lipids, essential proteins, oligosaccharides, immunomodulatory and metabolic factors necessary for infant growth and development, and also naturally reflects the developmental needs of newborns in terms of nutrition, which is essential for the short- and long-term development of infants. In view of this, breast milk is considered as a gold standard for the development of infant formula. In addition, infant formula is receiving increasing attentions in modern society due to growing research evidences showing that early dietary intake has a significant impact on the short- and long-term health of infants. Phospholipids are the main supports for the nutritional properties of milk fat globule membranes (MFGM), accounting for about 25% of MFGM components. Phospholipids are a large family that can be classified into glycerophospholipids and sphingolipids based on different head groups and backbones, wherein glycerophospholipids include phosphatidylcholine (PC), phosphatidylethanolamine (PE), phosphatidylinositol (PI), phosphatidylserine (PS), phosphatidylglycerol (PG), and phosphatidic acid (PA), and sphingolipids include sphingomyelin (SM) and ceramides (Cer); and they are further classified into different molecular species based on differences in fatty acyl chains. Phospholipids have many benefits for the healthy growth of infants, such as promoting neurological and cognitive development, regulating gastrointestinal lipid metabolism, modulating intercellular signaling, constructing a more efficient fat globule structure, while ensuring the stability of emulsions, or the like. These features are closely related to phospholipid head groups, backbones, the fatty acyl chain composition, and the content of phospholipids. The composition and content of phospholipids in breast milk are influenced by diet, lactation, genes and region, whereas those in infant formulas are mainly influenced by phospholipid-related supplements and processing.

Throughout the development history of infant formula lipids, infant formula in the simulation of breast milk lipids mainly focuses on the application of vegetable oils, the simulation of structural lipids and the supplementation of functional fatty acids, i.e., to achieve a closer match in the composition, content and structure of glycerol acids. However, the simulation of breast milk phospholipids has been gradually emphasized only as the specific characteristics of the membrane structure of breast milk fat globules have been gradually deduced and the important efficacy value of phospholipids has been verified. However, the evaluation method for the similarity of phospholipid simulations in infant formula has been rarely reported. In China, the vast majority of infant formulas are based on fresh milk or milk powder, and lipid moieties are made up of a combination of milk fats, vegetable oils and breast milk substitutes in milk or milk powder to simulate breast milk lipids. The composition and content of phospholipids in formulas are directly determined by the raw and auxiliary materials used in the processing of infant formulas however, the method for evaluating the similarity of raw and auxiliary materials based on lipids to breast milk has not been reported.

So far, evaluations on lipids in infant formulas and their raw and auxiliary materials have been mostly performed by employing chromatography and mass spectrometry to determine their data, and performing a comparative analysis to show the gap between lipids in infant formulas raw and auxiliary materials, and breast milk substitutes and lipids in breast milk. Previous evaluation techniques have mostly focused on assessment and comparison on the level of fatty acids or lipid subclasses, or on the level of a certain glyceride, without considering either the influence of the composition, content and form of phospholipids on infant formulas or the weighting of different species of phospholipids.

In view of this, the present invention is provided.

SUMMARY OF THE INVENTION

The present invention is directed to provide a method for evaluating the similarity of a dairy sample or a lipid sample to breast milk in a comprehensively detailed and multidimensional way, taking breast milk as a gold standard.

In order to achieve the above object, the present invention provides a method for multidimensional evaluation of the similarity of a sample to breast milk, the method being performed in the following steps:

(1) establishing a local breast milk phospholipid database;

(2) collecting and pretreating a sample to be evaluated;

(3) determining the contents of characteristic phospholipid subclasses, the contents of characteristic phospholipid molecules in the sample to be evaluated, and obtaining a microstructural image of milk fat globules in the sample by confocal laser scanning microscopy;

(4) calculating the score G for the sample to be evaluated according to the following formula:

$$G = G_s + G_m + G_p;$$

wherein, $$G_s = 100 - \sum \left( 100 \times \frac{H_i}{H_t} \times \frac{|H_{ih/l} - A_i|}{A_i} \right);$$

in the formula, $$H_{ih/l} = \begin{cases} 1.5H_i, \ A_i > 1.5H_i \\ A_i, \ 1.5H_i \geq A_i \geq 0.5H_i \ ; \\ 0.5H_i, \ A_i < 0.5H_i \end{cases}$$

wherein, $H_i$ is the content of the characteristic phospholipid subclass i in breast milk, $H_t$ is the total content of phospholipids in breast milk, and $A_i$ is the content of the characteristic phospholipid subclass i in the sample;

$$G_m = R_i \times \left\{ 100 - \sum \left( 100 \times \frac{H_n}{H_t} \times \frac{|H_{nh/l} - A_n|}{A_n} \right) \right\};$$

in the formula, $$H_{nh/l} = \begin{cases} 1.5H_n, & A_n > 1.5H_n \\ A_n, & 1.5H_n \geq A_n \geq 0.5H_n \; ; \\ 0.5H_n, & A_n < 0.5H_n \end{cases}$$

wherein, $R_i$ is a correction factor for phospholipids, i.e., the sum of the percentages of the contents of the characteristic phospholipid molecules in the sample in common with breast milk, $H_n$ is the content of the characteristic phospholipid molecule n in breast milk, $H_t$ is the total content of phospholipids in breast milk, and $A_n$ is the content of the characteristic phospholipid molecule n in the sample;

$G_p$ is a fuzzy evaluation score for the similarity of the microstructural image of milk fat globules in the sample to that of milk fat globules in breast milk.

Preferably or alternatively, in step (2), the pretreating is carried out as follows:

diluting an internal standard with a redissolving solution so that the concentration of the internal standard is consistent with that of breast milk, adding an internal standard to the sample, then adding ultrapure water, methanol and dichloromethane, mixing the above materials, and then adding ultrapure water and dichloromethane, centrifuging the mixed solution to separate an organic phase from an aqueous phase, adding ultrapure water, methanol and dichloromethane into the organic phase, evenly mixing, then centrifuging the mixed solution to separate an organic phase from an aqueous phase, merging the aqueous phases obtained after the two centrifugations, adding dichloromethane, mixing and centrifuging the mixed solution to separate an organic phase from an aqueous phase; and merging the organic phases obtained after the last two centrifugations, blowing the organic phases to be dried with nitrogen, and then redissolving the dried organic phases with the redissolving solution to obtain a sample to be extracted, which is then passed through a solid-phase extraction column to obtain a polar lipid separation solution.

Preferably or alternatively, the redissolving solution used in the pretreating is a methanol-dichloromethane solution containing 5-20 mM ammonium acetate, and a volume ratio of methanol to dichloromethane in the redissolving solution is 1:1-2.

Preferably or alternatively, the redissolving solution is a methanol-dichloromethane solution containing 10 mM ammonium acetate, and a volume ratio of methanol to dichloromethane in the redissolving solution is 1:1.

Preferably or alternatively, the internal standard is a standard of PC17:0-14:1, PE17:0-14:1, SM d18:1-17:0, PI17:0-14:1, PG17:0-14:1, Cer d18:2-24:0, which has a final concentration of 0.1-0.8 mg/L after addition.

Preferably or alternatively, passing through the solid-phase extraction column is performed as follows: adding the sample to be extracted to a silica gel column activated by n-hexane and standing for adsorption, then adding a mixture of n-hexane/diethyl ether in a volume ratio of 8:2 for elution, followed by adding a mixture of n-hexane/diethyl ether in a volume ratio of 1:1 for elution, combining and discarding the eluent, and then adding methanol and a mixture of dichloromethane/methanol/water in a volume ratio of 3:5:2 successively, collecting the eluent, which is then dried with nitrogen and dissolved with the redissolving solution to obtain the polar lipid separation solution.

Preferably or alternatively, in step (3), the method for determining the contents of the characteristic phospholipid subclasses and the characteristic phospholipid molecules is an ultra-high performance liquid chromatography tandem quadrupole time-of-flight mass spectrometry.

Preferably or alternatively, the ultra-high performance liquid chromatography is performed under the following conditions: injection volume: 2 μL; flow rate: 0.8 mL/min; column temperature: 30° C.; mobile phase A: a solution of 5 mM ammonium acetate in water/methanol/acetonitrile (1:1:1, v/v/v); mobile phase B: a solution of 5 mM ammonium ethanol in isopropanol; elution gradient:

| Phospholipids (Time, min) | 0.0 | 1.0 | 10.0 | 15.0 | 20.0 |
|---|---|---|---|---|---|
| A | 50% | 2% | 2% | 50% | 50% |
| B | 50% | 98% | 98% | 50% | 50%. |

Preferably or alternatively, the quadrupole time-of-flight mass spectrometry is performed under the following conditions: under the condition of positive and negative poles, ion source spray voltage: 5500 V and −4500 V, respectively; ion source gas pressure: 60 psi; ion source temperature: 650° C.; curtain gas pressure: 35 psi, de-clustering voltage: 80 V and −80 V, respectively; collision energy: 10 V and −10 V, respectively; scanning range: 50-1300 Da.

Preferably or alternatively, in step (3), the characteristic phospholipid subclasses comprise PE, PC, PI, PS, PA, PG, SM, and CER.

Preferably or alternatively, in step (3), the characteristic phospholipid molecules comprise SM42:2:2, PE36:2, SM40:1:2, PC36:2, PE36:1, SM38:1:2, SM36:1:2, SM34:1:2, SM42:1:2, PC34:1, PC34:2, PE34:1, PI36:2, PE38:4, PS36:2, PE36:3, PC34:0, LPE18:0, PE38:1, PI38:4, PE34:2, Cer42:2:2, SM40:2:2, PC36:3, PE34:0, PE38:3, PE40:6, PS36:1, PE38:2, PE40:4, PE32:1, SM40:0:2, PC36:1, PC38:4, PS36:0, PE40:5, Cer40:2:2, PC32:0, PE32:0, SM36:0:2, SM32:1:2, PI36:1, SM38:0:2, PI38:3, PI34:1, PC36:4, SM42:1:3, LPE16:0, PE40:1, LPE18:2, PE40:2, PE38:5, PE36:4, PE34:3, PE36:0, PI34:0, SM42:0:3, LPE18:1, LPI18:0, SM42:0:2, Cer38:0:3, SM38:2:2, and PI36:3.

Preferably or alternatively, the microstructural image in step (3) comprises a Nile red stained image and an Rd-DOPE stained image.

The present invention evaluates the similarity of samples to breast milk based on phospholipids in three aspects: the composition of characteristic phospholipid subclasses, the composition of characteristic phospholipid molecules, and the morphological similarity evaluation, so that the scheme can better evaluate the simulation quality of infant formulas and their raw and auxiliary materials to breast milk based on phospholipids.

DETAILED DESCRIPTION OF THE INVENTION

Figure 1:
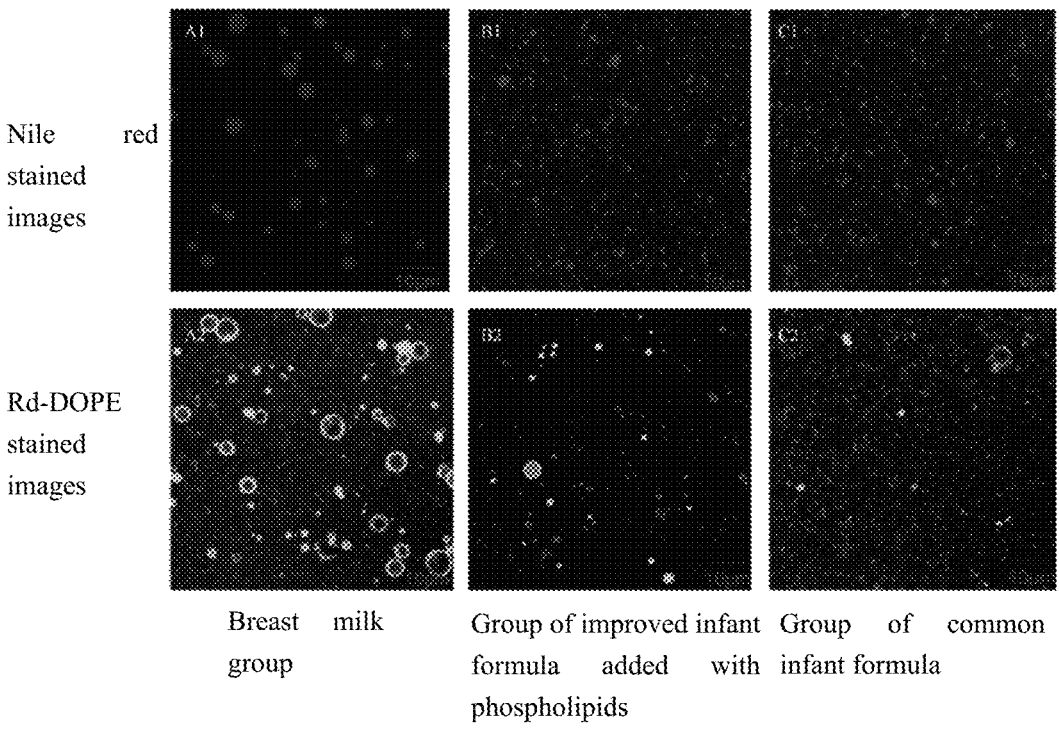
FIG. 1 shows Nile red stained images and Rd-DOPE stained images of the breast milk standard BF group, the common infant formula FF1 group and the improved infant formula FF2 group added with phospholipids in Example 2.

Specific embodiments of the present invention are described in detail below. It will be understood that the specific examples described herein are only used to explain the present invention, and are not intended to limit the present invention.

The experimental methods used in the following examples are conventional if not otherwise stated.

The materials and reagents used in the following examples are conventionally available, unless otherwise specified.

Example 1

This example provides a method for establishing a local breast milk database.

61 healthy lying-in women from Beijing, Tangshan, Liuyang and Luoyang were selected, and the relevant physical indicators of each lying-in woman were normal, and infants were all born at term.

A total of 233 breast milk samples aged 0-6 months were traced and collected from the 61 healthy lying-in women mentioned above, and the infant development status corresponding to each breast milk sample was recorded at the same time.

The samples were pretreated as follows before subjecting to chromatography and mass spectrometry: diluting the standard to a concentration similar to that of breast milk with a redissolving solution, which was a solution of methanol: dichloromethane (1:1, v/v) containing 10 mM ammonium acetate. 20 μL of 9.64 mg/L PE14:1-17:0, 20 μL of 10.38 mg/L PC14:1-17:0, 20 L of 10.00 mg/L SM d18:1-17:0, 8 μL of 10.22 mg/L PI14:1-17:0, 4 μL of 9.81 mg/L PG14:1-17:0 and 4 μL of 10.00 mg/L Cer d18:2-24:0 standards were added as an internal standard to 200 μL of the sample to be evaluated, followed by adding 200 μL of ultrapure water, 2 mL of methanol, and 900 μL of dichloromethane and mixing well, and then 200 μL of ultrapure water and 900 μL of dichloromethane were added and mixed well, and the mixture was centrifuged for 15 min at 6,000 rpm to separate an organic phase from an aqueous phase. 1 mL of ultrapure water, 2.2 mL of methanol and 600 μL of dichloromethane were added to the organic phase, and the mixture was centrifuged at 3000×g for 10 min to separate an organic phase from an aqueous phase. The aqueous phases were combined and mixed with 1.8 mL of dichloromethane, and the mixture was centrifuged for 15 min at 6,000 rpm to separate an organic phase from an aqueous phase, followed by combining the organic phases. The organic phases were dried with nitrogen and redissolved with 1 mL of a redissolving solution to obtain a sample to be extracted.

1 mL of the sample to be extracted was poured into a silica gel column (ProElut Silica (1 g/6 mL CAT NO:63006)) that had been activated by 3 mL of n-hexane with the eluent being discarded, followed by standing for 5 min for adsorption, after the adsorption was completed, 3 mL of n-hexane/diethyl ether (8:2, v/v) and 3 mL of n-hexane/diethyl ether (1:1, v/v) were added sequentially with the eluent being discarded, then 4 mL of methanol, 2 mL of methanol and 2 mL of a mixture of dichloromethane/methanol/water (3:5:2, v/v/v) were added sequentially, the eluents were collected and combined, dried with nitrogen gas, and then redissolved with 200 μL of a redissolving solution, to obtain a polar lipid separation solution for subsequent analysis.

The species and contents of phospholipids in the above breast milk samples were determined by employing an ultra-high performance liquid chromatography/quadrupole time-of-flight mass spectrometry (UPLC/Q-TOF-MS) with an ESI electrospray ion source and Peakview 2.2 and MSDIAL 3.20 data processing systems.

The specific chromatographic conditions were as follows: column: Phenomenex 2.6 μm C18 100 Å 150×4.6 mm, Kinetex; injection volume: 2 μL; flow rate: 0.8 mL/min; column temperature: 30° C.;

mobile phase A: a solution of 5 mM ammonium acetate in water/methanol/acetonitrile (1:1:1, v/v/v); mobile phase B: a solution of 5 mM ammonium ethanol in isopropanol;

The elution gradients were shown in Table 1:

TABLE 1

| Chromatographic elution gradients | | | | | |
|---|---|---|---|---|---|
| Time (min) | 0.0 | 1.0 | 10.0 | 15.0 | 20.0 |
| A | 50% | 2% | 2% | 50% | 50% |
| B | 50% | 98% | 98% | 50% | 50%. |

The quadrupole time-of-flight mass spectrometry was performed under the following conditions: under the condition of positive and negative poles, ion source spray voltage: 5500 V and −4500 V, respectively; ion source gas pressure: 60 psi; ion source temperature: 650° C.; curtain gas pressure: 35 psi, de-clustering voltage: 80 and −80 V, respectively; collision energy: 10 V and −10 V, respectively; scanning range: 50-1300 Da.

A sample prepared by taking equal volumes of the above 233 breast milk samples and mixing them was used as a breast milk standard, which was analyzed by the above chromatography and mass spectrometry method, and a total of 8 characteristic phospholipid subclasses and 63 main characteristic phospholipid molecules were detected, and the results were shown in Tables 2 and 3.

TABLE 2

| Results of the contents of eight characteristic phospholipid subclasses in the breast milk sample in Example 1: | |
|---|---|
| Characteristic phospholipid subclasses | Weight (%) |
| PE | 31.61 |
| PC | 17.28 |
| PI | 4.49 |
| PS | 3.10 |
| PA | 0.45 |
| PG | 0.19 |
| SM | 40.91 |
| CER | 1.98. |

TABLE 3

Results of the contents of the characteristic phospholipid
molecules in the breast milk sample in Example 1:

| Characteristic phospholipid molecules | Weight (%) |
| --- | --- |
| SM42:2; 2 | 10.31 |
| PE 36:2 | 9.83 |
| SM40:1; 2 | 9.73 |
| PC36:2 | 7.91 |
| PE36:1 | 6.13 |
| SM38:1; 2 | 5.49 |
| SM36:1; 2 | 4.41 |
| SM34:1; 2 | 4.19 |
| SM42:1; 2 | 3.67 |
| PC34:1 | 3.17 |
| PC34:2 | 2.49 |
| PE34:1 | 2.13 |
| PI36:2 | 2.05 |
| PE38:4 | 1.89 |
| PS36:2 | 1.73 |
| PE36:3 | 1.61 |
| PC34:0 | 1.41 |
| LPE 18:0 | 1.24 |
| PE38:1 | 1.18 |
| PI38:4 | 1.11 |
| PE34:2 | 1.08 |
| Cer42:2; 2 | 0.99 |
| SM40:2; 2 | 0.83 |
| PC36:3 | 0.79 |
| PE34:0 | 0.71 |
| PE38:3 | 0.66 |
| PE40:6 | 0.65 |
| PS36:1 | 0.64 |
| PE38:2 | 0.58 |
| PE40:4 | 0.52 |
| PE32:1 | 0.49 |
| SM40:0; 2 | 0.44 |
| PC36:1 | 0.44 |
| PC38:4 | 0.39 |
| PS36:0 | 0.38 |
| PE40:5 | 0.38 |
| Cer40:2; 2 | 0.35 |
| PC32:0 | 0.34 |
| PE32:0 | 0.32 |
| SM36:0; 2 | 0.31 |
| SM32:1; 2 | 0.30 |
| PI36:1 | 0.30 |
| SM38:0; 2 | 0.27 |
| PI38:3 | 0.26 |
| PI34:1 | 0.23 |
| PC36:4 | 0.22 |
| SM42:1; 3 | 0.22 |
| LPE16:0 | 0.21 |
| PE40:1 | 0.21 |
| LPE18:2 | 0.20 |
| PE40:2 | 0.19 |
| PE38:5 | 0.19 |
| PE36:4 | 0.17 |
| PE34:3 | 0.16 |
| PE36:0 | 0.15 |
| PI34:0 | 0.14 |
| SM42:0; 3 | 0.13 |
| LPE18:1 | 0.13 |
| LPI18:0 | 0.11 |
| SM42:0; 2 | 0.11 |
| Cer38:0; 3 | 0.11 |
| SM38:2; 2 | 0.11 |
| PI36:3 | 0.10 |
| others | 2.79. |

It should be noted that the item of others in Table 3 is the sum of the contents of phospholipid molecules other than the 63 characteristic phospholipid molecules described above, such as PC36:4, PE40:3, PG36:2, PS38:5, which are not listed in this example entirely.

That is, all subsequent analyses on other milk samples are evaluated on the basis of the contents of the characteristic phospholipid subclasses and the characteristic phospholipid molecules in the breast milk standard described above.

It should be noted, however, that due to differences in dietary and living habits in different regions, the compositions and contents of phospholipids in breast milks of healthy parturient women vary with different regions, and therefore, for those skilled in the art, the source of the breast milk sample may be selected according to actual needs, and correspondingly, the determination results of the characteristic phospholipid subclasses and characteristic phospholipid molecules in the breast milk standard prepared from the breast milk sample may vary accordingly.

A microstructural image of milk fat globules in the sample was obtained by using confocal laser scanning microscopy (CLSM) in this example. Specifically, Nile Red (NR) was dissolved in ethanol to prepared to an NR staining solution at a concentration of 42 mg/L; N-(lissamine rhodamine B sulfonyl) dioleoyl-phosphatidyl-ethanolamine (Rd-DOPE) was dissolved in chloroform to prepared to an Rd-DOPE staining solution at a concentration of 1 g/L. Wherein, the NR staining solution was used to label neutral lipids and the Rd-DOPE staining solution was used to label phospholipids in the sample.

10 μL of the NR staining solution or 2 μL of the Rd-DOPE staining solution were added to 100 μL of an unpretreated sample, respectively, followed by incubating at room temperature for 30 min, 10 μL of the mixture was taken and transferred to a microslide, and observed by using a confocal laser scanning microscope to obtain the microstructural image of milk fat globules in the sample.

Example 2

The scores of each sample were evaluated based on the contents of the characteristic phospholipid subclasses and the contents of the characteristic phospholipid molecules in the breast milk standard, as well as the microstructural image of milk fat globules in the sample described in Example 1.

The score G was calculated according to the formula below:

$$G = G_s + G_m + G_p;$$

wherein, $$G_s = 100 - \sum \left( 100 \times \frac{H_i}{H_t} \times \frac{|H_{ih/l} - A_i|}{A_i} \right);$$

in the formula, $$H_{ih/l} = \begin{cases} 1.5H_i, & A_i > 1.5H_i \\ A_i, & 1.5H_i \geq A_i \geq 0.5H_i \; ; \\ 0.5H_i, & A_i < 0.5H_i \end{cases}$$

wherein, $H_i$ is the content of the characteristic phospholipid subclass i in breast milk, $H_t$ is the total content of phospholipids in breast milk, and $A_i$ is the content of the characteristic phospholipid subclass i in the sample;

$$G_m = R_i \times \left\{ 100 - \sum \left( 100 \times \frac{H_n}{H_t} \times \frac{|H_{nh/l} - A_n|}{A_n} \right) \right\};$$

in the formula, $$H_{nh/l} = \begin{cases} 1.5H_n, & A_n > 1.5H_n \\ A_n, & 1.5H_n \geq A_n \geq 0.5H_n \; ; \\ 0.5H_n, & A_n < 0.5H_n \end{cases}$$

wherein, $R_i$ is a correction factor for phospholipids, i.e., the sum of the percentages of the contents of the characteristic phospholipid molecules in the sample in common with breast milk, $H_n$ is the content of the characteristic phospholipid molecule n in breast milk, $H_t$ is the total content of phospholipids in breast milk, and $A_n$ is the content of the characteristic phospholipid molecule n in the sample;

$G_p$ is a fuzzy evaluation score for the similarity of the microstructural image of milk fat globules in the sample to that of milk fat globules in breast milk.

Wherein, both $A_i$ and $A_n$ were determined by the same method as for the breast milk sample in Example 1.

The method for determining the similarity fuzzy evaluation score $G_p$ was performed by: taking photographs of milk fat globules of the breast milk standard stained with Nile Red and Rd-DOPE, respectively, at the same resolution (10 μm) and the corresponding photographs of the samples (shown in FIG. 1); and selecting ten persons for making similarity assessment, which make evaluation on morphological similarity between the photographs of the samples and those of breast milk using as a standard.

Assessment domain $U=(U_1, U_2, U_3)=$(morphology, quantity, area), comment domain $V=(V_1, V_2, V_3, V_4)=$(Basically the same, approximate, some differences, great differences) $=(100, 80, 60, 40)$, and the weight vector $X=(0.4, 0.3, 0.3)$. An evaluation matrix is created based on the above domains and the corresponding scores are calculated for the photographs of Nile Red- and Rd-DOPE-stained samples, respectively, which are summed and multiplied by a weighting factor to obtain a score for morphological similarity, which is incorporated into the scheme to calculate a total score.

The fuzzy mathematics sensory evaluation method in the present invention is performed in three steps:

(1) making statistics on the sensory evaluation results of the assessment domain and creating an assessment relationship matrix $C_i=(C_{i1}\; C_{i2}\; C_{i3}\; C_{i4})$ and a fuzzy evaluation matrix $$C = \begin{pmatrix} C_{morphology} \\ C_{quantity} \\ C_{area} \end{pmatrix}.$$

Based on the photographs, 10 persons make evaluation on similarity and make statistics on the statistical results for evaluating the morphology, quantity and area of milk fat globules, here, taking improved infant formula added with phospholipids as an example:

$C_{morphology}=(0.1\; 0.2\; 0.5\; 0.2)$, $$C = \begin{pmatrix} 0.1 & 0.1 & 0.5 & 0.3 \\ 0 & 0.1 & 0.4 & 0.5 \\ 0.1 & 0.1 & 0.2 & 0.6 \end{pmatrix}$$

where, i denotes morphology, quantity and area, (2) evaluating the result vector $B_k=(B_{k1}\; B_{k2}\; B_{k3}\; B_{k4})=X\times C=(X_1\; X_2\; X_3)C$, i.e., $$B_k = (0.4 \;\; 0.3 \;\; 0.3) \begin{pmatrix} 0.1 & 0.1 & 0.5 & 0.3 \\ 0 & 0.1 & 0.4 & 0.5 \\ 0.1 & 0.1 & 0.2 & 0.6 \end{pmatrix} = (0.07 \;\; 0.1 \;\; 0.38 \;\; 0.45)$$

(3) comprehensive score $G_p=V\times B_k^T=(V_1\; V_2\; V_3\; V_4)(B_{k1}\; B_{k2}\; B_{k3}\; B_{k4})^T$, i.e., $$G_p = (100 \;\; 80 \;\; 60 \;\; 40)(0.07 \;\; 0.1 \;\; 0.38 \;\; 0.45)^T = 55.8$$

wherein, the weights of morphology, quantity and area of milk fat globules are determined by selecting the averages of the scoring results from three methods: a forced scoring method, a link relative ratio scoring method and a statistical scoring method, as the final weights.

The scores of the exemplary improved infant formula added with phospholipids and the common infant formula calculated according to the above method are shown in the table below.

Among them, the improved infant formula added with phospholipids is commercially available from stage 1 milk powder added with MFGM under a certain brand, and the common infant formula is commercially available from stage 1 milk powder without MFGM under a certain brand.

TABLE 4

| Evaluation scores for each sample | |
| --- | --- |
| Milk Sample | Score (G) |
| Improved infant formula added with phospholipids | 149.93 |
| common infant formula | 121.34. |

It should be noted, however, that although only the above two infant formula were evaluated as examples in the example, the method according to the present invention is applicable not only to the evaluation of infant formula, but also to the evaluation of fat-based raw materials as raw and auxiliary materials, and various dairy products.

Example 3

This example scores an actual sample using the method described in Example 2 and validates the score from a nutritional perspective.

The dairy samples in this example are selected to be the common infant formula (FF1) and the improved formula added with phospholipids (FF2) involved in Example 2.

The scores for FF1 and FF2 obtained by calculation in Example 2 are 121.34 and 149.93, respectively.

Nutrition verification was performed by using an animal experiment. 5 pregnant British white binary hybrid sows with similar maternal ages were selected. SPF piglets (n=20) born naturally were naturally delivered SPF sows. Healthy piglets with similar weight and length were selected, and breastfed uniformly within 3 days after birth to provide sufficient maternal immunity and nutrition for the piglets. Breastfeeding was conducted for 3 days prior to the start of the experiment, and then the feeding experiment was officially conducted until 31 days. After the formal experiment began, the experiment was randomly divided into three groups: breast milk group (BF group), FF1 group and FF2 group. The piglets and sows in breast milk group were managed in the same pigsty and continued breastfeeding until 31 days of weaning; the infant formula groups were fed with reconstituted milk made of milk powder and water by using feeding bottles (later in a feeding trough) until 31 days. During this period, piglets were separated from sows and managed separately in cages. The samples were collected on the 31 d after delivery.

Fecal samples were collected as follows: about 10 g of feces from piglets were collected on the 7th, 14th and 21st day of feeding, quickly frozen in liquid nitrogen, transported with dry ice, and then stored in a refrigerator at a low temperature of –80° C. for later use.

An intestinal flora 16S rRNA gene was detected through high-throughput sequencing. Genomic DNA was extracted from 100 mg of fecal samples using a QIAamp Rapid Fecal DNA Mini kit (Qiagen, GmbH, Hilden, Germany) according to the kit instructions. PCR was then performed to amplify 16S rRNA gene in V3-V4 region using 10 ng of DNA as a template. 30 µL of the total reaction system comprised of: 15

µL of high-fidelity PCR reaction mixture (New England Biolabs), and 0.2 µM positive and reverse primers (314F-805R). PCR conditions were as follows: 95° C. for 3 min; 25 cycles for 30 s: 95° C., 30 s; 30 s, 55° C., and 30 s, 72° C. Sequencing libraries were constructed using a NEB Ultra DNA library preparation kit (NEB, USA) according to the instructions. Amplicon sequencing was performed with PE 2×250 bp HiSeq 2500 (Illumina, USA). Original offline sequencing data were merged, quality screened and demultiplexed using QIIME 1.9.0. Sequences were clustered and those with 97% similarity were grouped into operational taxonomic units (OTUs), and then the OTU sequences were performed with species annotation classification from phylum to genus based on the Greengenes 16S rRNA gene database (Version 13.5). Downstream data analysis was performed by using R language, including α-diversity, and β-diversity analysis using Bray-Curtis distance or UniFrac distance, and the like, and the results are shown in Table 5.

TABLE 5

| | Kruskall-Wallis test | | Generalized linear model (GLM) | | Median abundance | | |
| | | | | | Common infant | Infant formla added with | breast |
| Bacteria | kw.ep | kw.eBH | glm.ep | glm.eBH | formula | phospholipids | milk |
|---|---|---|---|---|---|---|---|
| Phylum, 7 d | | | | | | | |
| not detected | — | — | — | — | — | — | — |
| Phylum, 14 d | | | | | | | |
| Actinobacteria | 0.010853 | 0.043411 | 0.00318 | 0.012763 | 10 | 102 | 7 |
| Proteobacteria | 0.00315 | 0.023741 | 0.000135 | 0.000919 | 785 | 929.5 | 4535 |
| Phylum, 21 d | | | | | | | |
| Actinobacteria | 0.040421 | 0.173258 | 0.008523 | 0.040952 | 15 | 30 | 179.5 |
| Proteobacteria | 0.023896 | 0.165225 | 0.003911 | 0.028822 | 827 | 2251 | 7716 |
| Genus, 7 d | | | | | | | |
| Parabacteroides | 0.0075 | 0.160763 | 0.001829 | 0.036809 | 735.5 | 392 | 53.5 |
| Bilophila | 0.015334 | 0.187366 | 0.008836 | 0.068471 | 21 | 2 | 0 |
| Eubacterium | 0.015645 | 0.183573 | 0.002347 | 0.035756 | 19 | 26 | 2.5 |
| Lactobacillus | 0.024456 | 0.203986 | 0.004763 | 0.055076 | 1234 | 296 | 5.5 |
| Fusobacterium | 0.033069 | 0.23279 | 0.034268 | 0.142435 | 15 | 545 | 679 |
| Genus, 14 d | | | | | | | |
| Catenibacterium | 0.001622 | 0.03942 | 3.89E–06 | 0.000162 | 228 | 1557 | 1 |
| Dorea | 0.002349 | 0.03942 | 8.25E–05 | 0.001105 | 26 | 47 | 432 |
| Anaerovibrio | 0.002863 | 0.040585 | 0.000155 | 0.001897 | 5 | 306 | 0 |
| Parabacteroides | 0.002944 | 0.040861 | 4.47E–05 | 0.000801 | 189 | 115.5 | 1001 |
| Collinsella | 0.003751 | 0.043296 | 0.001337 | 0.009061 | 7 | 101 | 0 |
| Clostridium | 0.008934 | 0.069456 | 0.001231 | 0.008981 | 9 | 7.5 | 735 |
| Bulleidia | 0.011679 | 0.07115 | 0.017382 | 0.045802 | 8 | 43 | 0 |
| Desulfovibrio | 0.01495 | 0.085093 | 0.006087 | 0.028499 | 72 | 67 | 225 |
| Faecalibacterium | 0.016227 | 0.085755 | 0.005319 | 0.025666 | 55 | 86 | 0 |
| Butyricimonas | 0.019845 | 0.097577 | 0.005699 | 0.028187 | 28 | 16 | 140 |
| Unclassified Erysipelotrichaceae | 0.020902 | 0.092181 | 0.006033 | 0.022019 | 2 | 2 | 56 |
| Unclassified Clostridiaceae | 0.026615 | 0.116349 | 0.001513 | 0.011062 | 81 | 5 | 138 |
| Coprobacillus | 0.037547 | 0.124386 | 0.025786 | 0.068567 | 30 | 0 | 1 |
| Bacteroides | 0.041893 | 0.145959 | 0.026109 | 0.09091 | 3166 | 1164.5 | 3122 |
| Escherichia | 0.041979 | 0.140673 | 0.082801 | 0.181732 | 3 | 3 | 20 |
| Unclassified Enterobacteriaceae | 0.044442 | 0.147031 | 0.075075 | 0.189521 | 314 | 679.5 | 4195 |
| Unclassified Barnesiellaceae | 0.049226 | 0.153791 | 0.059893 | 0.122016 | 0 | 0 | 7 |
| Genus, 21 d | | | | | | | |
| Bilophila | 0.01134 | 0.135041 | 0.001142 | 0.008415 | 49 | 283 | 14.5 |
| Oxalobacter | 0.013455 | 0.135041 | 0.000905 | 0.005193 | 8 | 19 | 0.5 |
| Prevotella | 0.015353 | 0.135041 | 0.000282 | 0.00369 | 92 | 219 | 24.5 |

TABLE 5-continued

Results for intestinal flora abundance:

| | | | | | Median abundance | | |
| | Kruskall-Wallis test | | Generalized linear model (GLM) | | Common infant | Infant formla added with | breast |
| Bacteria | kw.ep | kw.eBH | glm.ep | glm.eBH | formula | phospholipids | milk |
|---|---|---|---|---|---|---|---|
| Unclassified Coriobacteriaceae | 0.016226 | 0.135041 | 7.14E–05 | 0.001285 | 0.5 | 1 | 120 |
| Catenibacterium | 0.019166 | 0.135041 | 0.000288 | 0.003453 | 198.5 | 79 | 1 |
| Clostridium | 0.019408 | 0.135041 | 0.000216 | 0.002602 | 1.5 | 4 | 556 |
| Dorea | 0.020009 | 0.135041 | 0.001544 | 0.010172 | 13.5 | 11 | 487.5 |
| Unclassified Mogibacteriaceae | 0.020034 | 0.135041 | 9.94E–06 | 0.000445 | 9 | 11 | 568.5 |
| Enterococcus | 0.020883 | 0.136594 | 0.002141 | 0.010969 | 0.5 | 0 | 139.5 |
| Coprococcus | 0.0271 | 0.141774 | 0.005562 | 0.020127 | 33.5 | 23 | 0 |
| Pseudoramibacter Eubacterium | 0.028363 | 0.145363 | 0.008101 | 0.027801 | 1 | 2 | 52.5 |
| Unclassified Enterobacteriaceae | 0.029138 | 0.142957 | 0.001433 | 0.010351 | 346.5 | 198 | 7472.5 |
| Desulfovibrio | 0.033946 | 0.149374 | 0.010548 | 0.039606 | 320.5 | 473 | 101 |
| Helicobacter | 0.037404 | 0.153828 | 0.004536 | 0.018023 | 6 | 5 | 0 |
| Faecalibacterium | 0.044821 | 0.15999 | 0.014105 | 0.043549 | 126 | 8 | 0 |
| Mogibacterium | 0.047376 | 0.168498 | 0.024355 | 0.058227 | 0 | 0 | 14 |
| Fusobacterium | 0.047618 | 0.163792 | 0.019083 | 0.056607 | 17.5 | 1 | 74 |
| Unclassified Bacteroidales | 0.048348 | 0.167441 | 0.010175 | 0.03802 | 349 | 152 | 25 |
| Alistipes | 0.049611 | 0.168682 | 0.022136 | 0.05596 | 1 | 4 | 0 |

As can be seen from Table 5, at the phylum level, *Actinobacillus* and *Proteus* show higher abundance in the breastfed piglets, followed by the phospholipids-added infant formula-fed piglets, and then the standard formula-fed piglets (0.05). However, there is no significant flora difference among the three groups during 7 days. At the genus level and the age of 7 days, *Bacteroides*, Bilophila and *Lactobacillus* in the two infant formula groups are higher than those in the breast milk group, *Clostridium* is higher in milk powder groups, and *Eubacterium* is also higher in infant formula groups than in the breast milk group; at age of 14 days, Dorea, *Bacteroides, Clostridium, Desulfovibrio*, Butyricimonas and Unclassified Enterobacteriaceae are higher in the breast milk group; Catenibacterium, Anaerovibrio, Collinsella, Bulleidia and *Bacteroides* are all higher in FF2 group; *Faecalibacterium* is higher in both infant formula groups, and only *Bacillus faecalis* is higher in FF1 group; at age of 21 days, *Clostridium*, Dorea, Unclassified Mogibacteriaceae, Pseudoramibacter *Eubacterium*, and Unclassified Enterobacteriaceae show higher abundance in the breast milk group, and Bilophila, Oxalobacter, *Prevotella*, and *Desulfovibrio* are higher in the piglets fed with the phospholipids-added infant formula group, whereas *Coprococcus* and Catenibacterium are higher in the piglets fed with common infant formula After the completion of 31 days of feeding, the tissue morphologies of the small intestine (duodenum, jejunum and ileum) and large intestine (colon) of 31-day-old piglets were determined, including the following determining index: intestinal tissue villus height, villus bottom width, villus middle width, villus top width, villus surface area and crypt depth, and the Kruskal-Wallis difference test was performed. Tissue sections are shown in FIG. 2, and the results of morphological index are shown in FIGS. 3-4.

Figure 2:
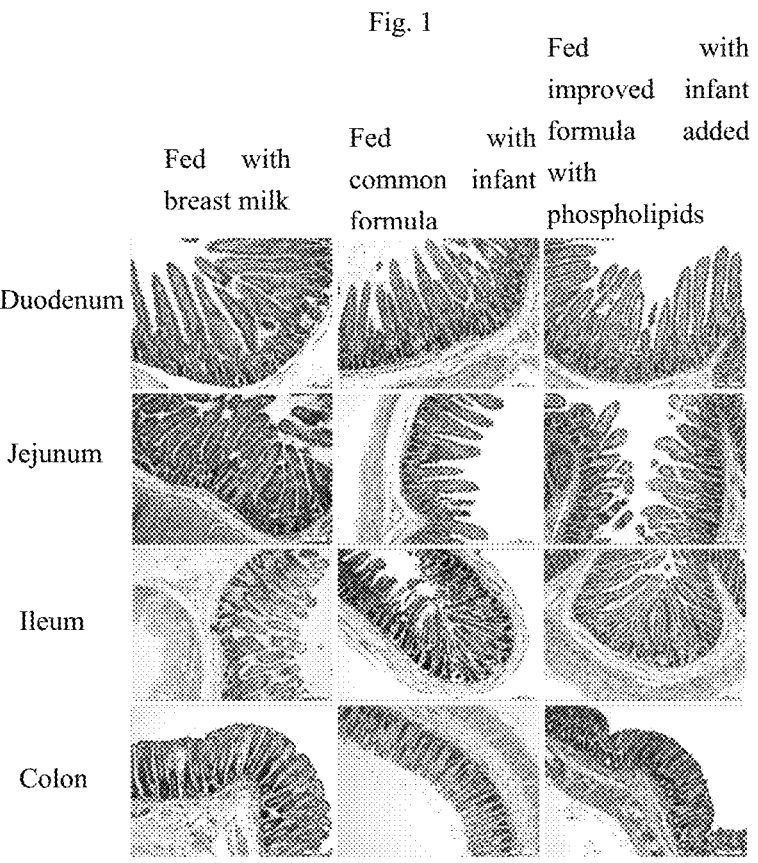
FIG. 2 shows morphological histological sections of intestinal tracts of piglets fed with different regimens in Example 3.
Figure 3:
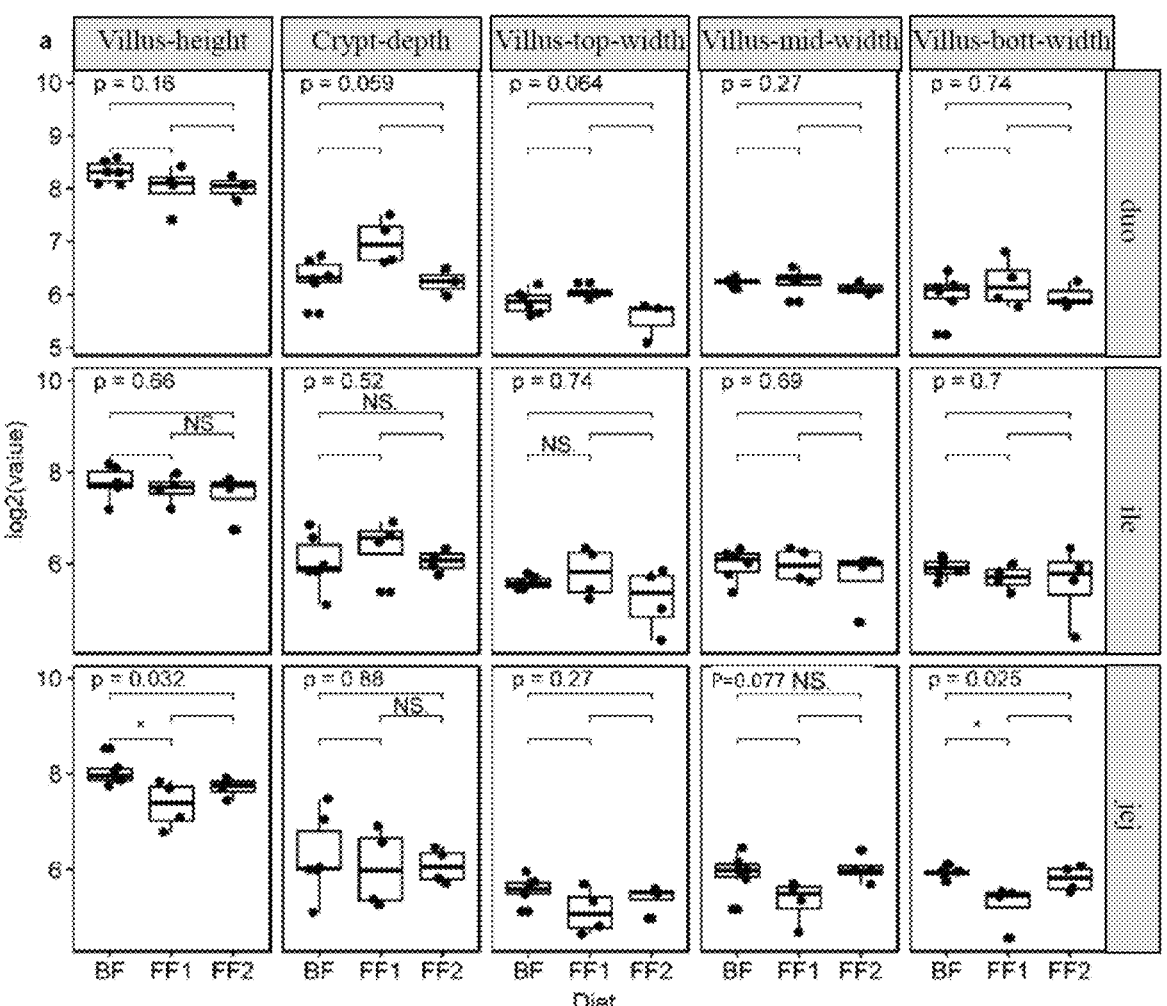
FIG. 3 shows morphological index maps of intestinal tracts of piglets fed with different regimens in Example 3.
Figure 4:
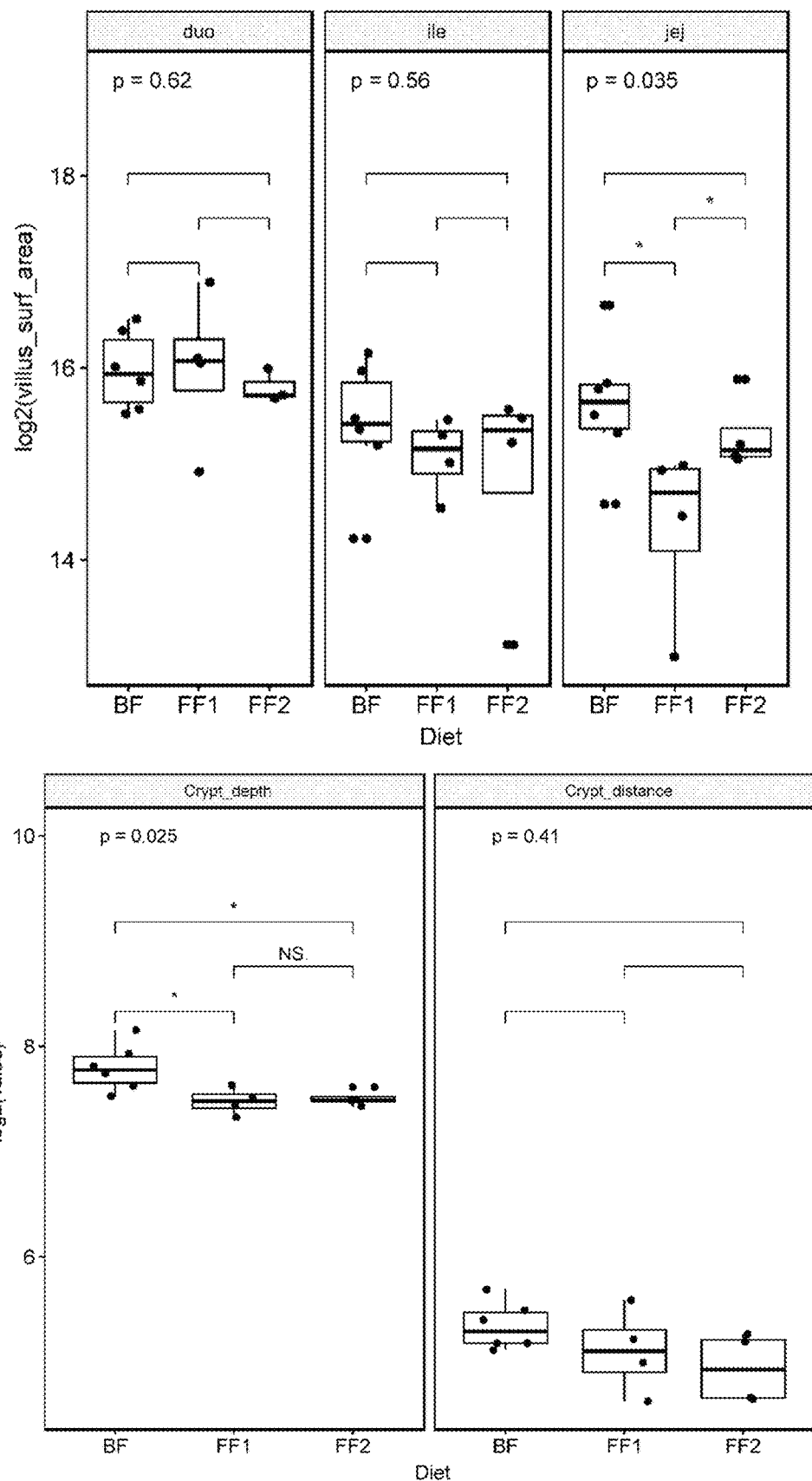
FIG. 4 shows morphological histological index maps of intestinal tracts of piglets fed with different regimens in Example 3.

As can be seen from FIGS. 2-4, the jejunal villus tissue morphology in the FF2 group is similar to that in the breast milk group, specifically, the villus height, villus base width and villus surface area of the jejunum are significantly higher in the breast milk group than in the FF1 group, at the same time, in the colon, the crypt depth in the FF2 group is similar to that in the breast milk group and is significantly higher than that in the FF1 group.

In summary, through the above experimental validation, the higher scoring FF2 group is fed to significantly increase the abundance of Bilophila, Oxalobacter, *Prevotella*, and *Desulfovibrio* in piglets, as well as the content of serum betaine, which are superior to those of the lower scoring FF1 group, and the development of the intestinal tract is significantly superior to that in the FF1 group, which is closer to that in the breast milk group.

The above results show that by adding phospholipid raw materials to infant formula, the composition of phospholipids therein is closer to breast milk, so that the resulting infant formula is more conducive to the immunity of the newborns, and can improve the composition of the intestinal microorganisms and the amino acid metabolism of the organism. That is to say, the results of the method provided by the present invention for multidimensional evaluation of the similarity of a sample to breast milk are reliable and valid, and the method is instructive for the dairy industry to further provide products having a higher similarity to breast milk.

Preferred embodiments of the present invention are described in detail above; however, the present invention is not limited to the specific details of the above embodiments, within the scope of the technical conception of the present invention, a variety of simple variants of the technical solution of the present invention may be performed, these simple variants are within the scope of protection of the present invention.

Further, any combination may be made between various embodiments of the present invention, as long as it does not contravene the concept of the present invention, it shall likewise be regarded as the disclosed content of the present invention.

The invention claimed is:

1. A method for multidimensional evaluation of the similarity of a sample to breast milk, comprising the following steps:

(1) establishing a local breast milk phospholipid database;

(2) collecting and pretreating a sample to be evaluated;

(3) determining the contents of characteristic phospholipid subclasses, the contents of characteristic phospholipid molecules in the sample to be evaluated, and obtaining a microstructural image of milk fat globules in the sample by confocal laser scanning microscopy;

(4) calculating the score G for the sample to be evaluated according to the following formula:

$$G = G_s + G_m + G_p;$$

wherein $$G_s = 100 - \sum\left(100 \times \frac{H_i}{H_t} \times \frac{|H_{ih/l} - A_i|}{A_i}\right);$$

in the formula, $$H_{ih/l} = \begin{cases} 1.5H_i, & A_i > 1.5H_i \\ A_i, & 1.5H_i \geq A_i \geq 0.5H_i \ ; \\ 0.5H_i, & A_i < 0.5H_i \end{cases}$$

wherein, $H_i$ is the content of the characteristic phospholipid subclass i in breast milk, $H_t$ is the total content of phospholipids in breast milk, and $A_i$ is the content of the characteristic phospholipid subclass i in the sample;

$$G_m = R_i \times \left\{100 - \sum\left(100 \times \frac{H_n}{H_t} \times \frac{|H_{nh/l} - A_n|}{A_n}\right)\right\};$$

in the formula, $$H_{nh/l} = \begin{cases} 1.5H_n, & A_n > 1.5H_n \\ A_n, & 1.5H_n \geq A_n \geq 0.5H_n \ ; \\ 0.5H_n, & A_n < 0.5H_n \end{cases}$$

wherein, $R_i$ is a correction factor for phospholipids, i.e., the sum of the percentages of the contents of the characteristic phospholipid molecules in the sample in common with breast milk, $H_n$ is the content of the characteristic phospholipid molecule n in breast milk, $H_t$ is the total content of phospholipids in breast milk, and $A_n$ is the content of the characteristic phospholipid molecule n in the sample;

$G_p$ is a fuzzy evaluation score for the similarity of the microstructural image of milk fat globules in the sample to that of milk fat globules in breast milk.

2. The method for multidimensional evaluation of the similarity of a sample to breast milk according to claim 1, wherein in step (2), the pretreating is carried out in the following steps: diluting an internal standard with a redissolving solution so that the concentration of the internal standard is consistent with that of breast milk, adding an internal standard to the sample, then adding ultrapure water, methanol and dichloromethane, mixing the above materials, and then adding ultrapure water and dichloromethane, centrifuging the mixed solution to separate an organic phase from an aqueous phase, adding ultrapure water, methanol and dichloromethane into the organic phase, evenly mixing, then centrifuging the mixed solution to separate an organic phase from an aqueous phase, merging the aqueous phases obtained after the two centrifugations, adding dichloromethane, mixing and centrifuging the mixed solution to separate an organic phase from an aqueous phase; and merging the organic phases obtained after the last two centrifugations, blowing the organic phases to be dried with nitrogen, and then redissolving the dried organic phases with the redissolving solution to obtain a sample to be extracted, which is then passed through a solid-phase extraction column to obtain a polar lipid separation solution.

3. The method for multidimensional evaluation of the similarity of a sample to breast milk according to claim 2, wherein, the redissolving solution used in the pretreating is a methanol-dichloromethane solution containing 5-20 mM ammonium acetate, and a volume ratio of methanol to dichloromethane in the redissolving solution is 1:1-2.

4. The method for multidimensional evaluation of the similarity of a sample to breast milk according to claim 3, wherein, the redissolving solution is a methanol-dichloromethane solution containing 10 mM ammonium acetate, and a volume ratio of methanol to dichloromethane in the redissolving solution is 1:1.

5. The method for multidimensional evaluation of the similarity of a sample to breast milk according to claim 2, wherein, the internal standard is a standard of PC 17:0-14:1, PE 17:0-14:1, SM d18:1-17:0, PI17:0-14:1, PG17:0-14:1, Cer d18:2-24:0, which has a final concentration of 0.1-0.8 mg/L after addition.

6. The method for multidimensional evaluation of the similarity of a sample to breast milk according to claim 2, wherein, passing through the solid-phase extraction column is performed as follows: adding the sample to be extracted to a silica gel column activated by n-hexane and standing for adsorption, then adding a mixture of n-hexane/diethyl ether in a volume ratio of 8:2 for elution, followed by adding a mixture of n-hexane/diethyl ether in a volume ratio of 1:1 for elution, combining and discarding the eluent, and then adding methanol and a mixture of dichloromethane/methanol/water in a volume ratio of 3:5:2 successively, collecting the eluent, which is then dried with nitrogen and dissolved with the redissolving solution to obtain the polar lipid separation solution.

7. The method for multidimensional evaluation of the similarity of a sample to breast milk according to claim 1, wherein in step (3), the method for determining the contents of the characteristic phospholipid subclasses and the characteristic phospholipid molecules is an ultra-high performance liquid chromatography tandem quadrupole time-of-light mass spectrometer.

8. The method for multidimensional evaluation of the similarity of a sample to breast milk according to claim 7, wherein, the ultra-high performance liquid chromatography is performed as follows: injection volume: 2 μL; flow rate: 0.8 mL/min; column temperature: 30° C.; mobile phase A: a solution of 5 mM ammonium acetate in water/methanol/acetonitrile (1:1:1, v/v/v); mobile phase B: a solution of 5 mM ammonium ethanol in isopropanol; elution gradient:

| Phospholipids (Time, min) | 0.0 | 1.0 | 10.0 | 15.0 | 20.0 |
|---|---|---|---|---|---|
| A | | 50% | 2% | 2% | 50% | 50% |
| B | | 50% | 98% | 98% | 50% | 50%. |

9. The method for multidimensional evaluation of the similarity of a sample to breast milk according to claim 7, wherein, the quadrupole time-of-flight mass spectrometry is performed under the following conditions: under the condition of positive and negative poles, ion source spray voltage: 5500 V and −4500 V, respectively; ion source gas pressure: 60 psi; ion source temperature: 650° C.; curtain gas pressure: 35 psi, de-clustering voltage: 80 V and −80 V, respectively; collision energy: 10 V and −10 V, respectively; scanning range: 50-1300 Da.

10. The method for multidimensional evaluation of the similarity of a sample to breast milk according to claim 1, wherein in step (3), the characteristic phospholipid subclasses comprise PE, PC, PI, PS, PA, PG, SM, and CER.

11. The method for multidimensional evaluation of the similarity of a sample to breast milk according to claim 1, wherein in step (3), the characteristic phospholipid molecules comprise SM42:2;2, PE36:2, SM40:1;2, PC36:2, PE36:1, SM38:1;2, SM36:1;2, SM34:1;2, SM42:1;2, PC34: 1, PC34:2, PE34:1, PI36:2, PE38:4, PS36:2, PE36:3, PC34: 0, LPE18:0, PE38:1, PI38:4, PE34:2, Cer42:2;2, SM40:2;2, PC36:3, PE34:0, PE38:3, PE40:6, PS36:1, PE38:2, PE40:4, PE32:1, SM40:0;2, PC36:1, PC38:4, PS36:0, PE40:5, Cer40:2;2, PC32:0, PE32:0, SM36:0;2, SM32:1;2, PI36:1, SM38:0;2, PI38:3, PI34:1, PC36:4, SM42:1;3, LPE16:0, PE40:1, LPE18:2, PE40:2, PE38:5, PE36:4, PE34:3, PE36: 0, PI34:0, SM42:0;3, LPE18:1, LPI18:0, SM42:0;2, Cer38: 0;3, SM38:2;2, and PI36:3.

12. The multidimensional evaluation method for the similarity of a sample to breast milk according to claim 1, wherein the microstructural image in step (3) comprises a Nile red stained image and an Rd-DOPE stained image.

* * * * *